United States Patent [19]
Smith et al.

[11] Patent Number: 5,107,034
[45] Date of Patent: Apr. 21, 1992

[54] METHOD FOR PRODUCING 4-(2'-METHOXYETHYL)PHENOL

[75] Inventors: Brad L. Smith, Portland; Werner H. Mueller, Corpus Christi, both of Tex.; Heinz Strutz, Frankfurt am Main, Fed. Rep. of Germany

[73] Assignee: Hoechst Celanese Corporation, Somerville, N.J.

[21] Appl. No.: 502,146

[22] Filed: Mar. 28, 1990

[51] Int. Cl.$^5$ .............................................. C07C 41/01
[52] U.S. Cl. .................................................. 568/662
[58] Field of Search ........................................ 568/662

[56] References Cited

U.S. PATENT DOCUMENTS 3,873,600 3/1975 Brandstrom .

OTHER PUBLICATIONS

J. Organic Chemistry (1964), vol. 29, pp. 3459-3461, "Selective Bromination with Copper(II) Bromide", C. King et al.
Methoden Der Organischen Chemie, "Vierte, Vollig Neu Gestaltete Auflage", p. 374, E. Muller & Otto Bayer (1980).
Journal Med. Chem., 1988, vol. 31, pp. 55-59, "Chemical Aspects of Metoprolol Metabolism. Asymmetric Synthesis & Absolute Configuration of the 3-[4-(1-Hydroxy-2-methoxyethyl)phenoxy]-1-(isopropylamino)-2-propanols", the Diastereomeric., Shetty et al.
Synthesis, Dec. 1988, pp. 966-968, "A Short Synthesis of Albuterol", Esther Babad et al.
Pharmaceutical Manufacturing Encyclopedia, vol. 2, pp. 1009-1010, "Metroprolol Tartrate", Marshall Sittig.
J.A.C.S. (1957), vol. 79, p. 756, "The Formation of Dienones Through Ar$_1$-Participation", S. Winstein et al.
Merck Index 10th edt., p. 6031, "Metroprolol".
J.A.C.S., vol. 85, p. 575, (1963), "Neighboring Carbon & Hydrogen, LI.[1].Dienones from Ar$_1$O-3 Participation. Isolation & Behavior of Spiro(2,5)octa-1,-4-diene-3-one".
J. Chem. Soc., (1954), pp. 1034-1038, "Halogenated o- and p-Phenolic Ketones", Ng. Ph. Buu-Hot et al.
Organometallics, vol. 5, No. 9 1986, pp.-1910-1911.
Basic Principles of Organic Chemistry, pp. 457-460, (1965) "Reduction of Carbonyl Compounds", John D. Roberts et al.

*Primary Examiner*—Marianne Cintins
*Assistant Examiner*—Margaret J. Argo
*Attorney, Agent, or Firm*—Richard S. Roberts

[57] ABSTRACT

The invention provides a method for producing 4-(2'-methoxyethyl)phenol by brominating 4-hydroxyacetophenone to produce alpha-bromo-5-hydroxyacetophenone, and then causing a methoxide-bromide exchange to thereby produce alpha-methoxy-4-hydroxyacetophenone; and then conducting a single step reduction of alpha-methoxy-4-hydroxyacetophenone with at least two equivalents of hydrogen per equivalent of alpha-methoxy-4-hydroxyacetophenone in the presence of a hydrogenation catalyst to thereby directly produce 4-(2'-methoxyethyl)phenol.

26 Claims, No Drawings

METHOD FOR PRODUCING 4-(2'-METHOXYETHYL)PHENOL

BACKGROUND OF THE INVENTION

The present invention relates to a method for producing 4-(2'-methoxyethyl) phenol, or more particularly to a method for producing 4-(2'-methoxyethyl) phenol from 4-hydroxyacetophenone. 4-(2'-methoxyethyl)-phenol is useful as an intermediate in the production of Metoprolol which is a beta-adrenergic blocker known as 1-[4-(2-methoxyethyl)phenoxy]-3-[(1-methoxyethyl)amino]-2-propanol. The manufacture of Metroprolol tartrate from 4-(2'-methoxyethyl)phenol is described in the Pharmaceutical Manufacturing Encyclopedia, volume 2, pages 1009-1010 as well as in U.S. Pat. No. 3,873,600, both of which are incorporated herein by reference.

4-(2'-methoxyethyl)phenol is not a new compound. Its production by complex mechanisms is shown in French patent 2,487,338; the Journal of the American Chemical Society, Vol. 85, p. 575 (1963) and the Journal of the American Chemical Society, vol 79, p. 756 (1957). French patent 2,487,338 starts with a brominated alkyloxy phenol which is then treated with a Grignard reagent to produce an organo-magnesium compound. This is then reacted with an aldehyde, acetate or nitrile to produce a secondary alcohol or ketone which is then treated with a mineral acid to produce, in the case closest to this invention, a methoxy-4-hydroxyacetophenone. This ketone is then hydrogenated to produce a carbinol which is then reacted with acetic anhydride and sodium acetate to obtain a vinyl ether. The vinyl ether is then catalytically hydrogenated to produce a methoxyethyl phenylacetate, which is then saponified to obtain 4-(2'-methoxyethyl)phenol. The present invention improves upon this complex procedure by providing the alpha-methoxy-4-hydroxyacetophenone in a technically much more feasible way and by directly and substantially completely hydrogenating alpha-methoxy-4-hydroxyacetophenone. As a general overview the method of this invention proceeds by brominating 4-hydroxyacetophenone, causing a methoxide-bromide exchange and conducting a single step reduction of the methoxy- para-hydroxyacetophenone to 4-(2'-methoxyethyl)phenol according to the reaction scheme:

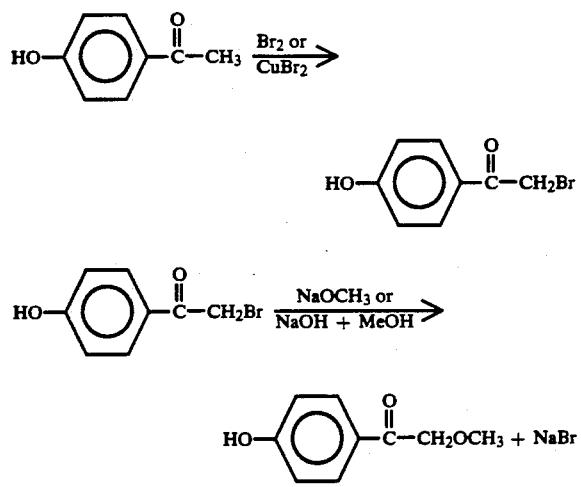

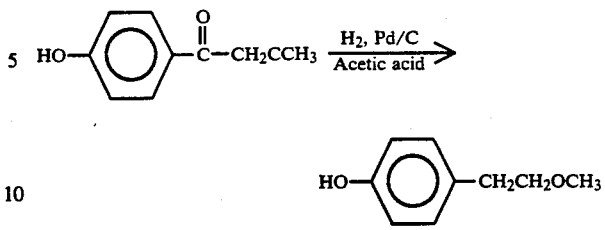

SUMMARY OF THE INVENTION

The invention provides a method for producing 4-(2'-methoxyethyl)phenol which comprises
a) brominating 4-hydroxyacetophenone to produce alpha-bromo-4-hydroxyacetophenone, and
b) causing a methoxide-bromide exchange to the alpha-bromo-4-hydroxyacetophenone to thereby produce alpha-methoxy-4-hydroxyacetophenone; and
c) conducting a single step reduction of alpha-methoxy-4-hydroxyacetophenone with at least two equivalents of hydrogen per equivalent of alpha-methoxy-4-hydroxyacetophenone in the presence of a hydrogenation catalyst to thereby directly produce 4-(2'-methoxyethyl)phenol in a major amount.

The invention also provides a method for producing 4-(2'-methoxyethyl)phenol which comprises
a) providing alpha-methoxy-4-hydroxyacetophenone; and
b) conducting a single step reduction of alpha-methoxy-4-hydroxyacetophenone with at least two equivalents of hydrogen per equivalent of alpha-methoxy-4-hydroxyacetophenone in the presence of a hydrogenation catalyst to thereby directly produce 4-(2'-methoxyethyl)phenol in a major amount.

DETAILED DESCRIPTION OF THE PREFERRED EMBODIMENT

The bromination of 4-hydroxyacetophenone is known in the art and may be performed by reacting 4-hydroxyacetophenone with either Br$_2$ or CuBr$_2$. King et al, *Selective Bromination with Copper (II) Bromide*, Journal of Organic Chemistry (1964) 29,3459 suggests adding 1 mole of 4-hydroxyacetophenone to a suspension of 2 moles of copper(II)bromide in refluxing chloroform-ethyl acetate. Alpha-bromo-4-hydroxyacetophenone is produced along with copper bromide and hydrogen bromide. Buu-Hai et al, *Halogenated o-and p-Phenolic Ketones*, Journal of the Chemical Society (1954), 1034 (at 1037) teaches one to add a solution of bromine in acetic acid to a stirred solution of 4-hydroxyacetophenone in acetic acid. After one hour at room temperature the mixture is concentrated in a vacuum and poured into water to form a precipitate which gradually solidifies into alpha-bromo-4-hydroxyacetophenone. Each of the foregoing articles is incorporated herein by reference.

The next step in the process is to cause a methoxide-bromide exchange in the alpha-bromo-4-hydroxyacetophenone to produce alpha-methoxy-4-hydroxyacetophenone. The exchange may be performed either by reaction of the bromo compound with an alkali metal methoxide or with methanol plus an alkali metal hydroxide, alkaline earth metal hydroxide or alkali metal sulfonate. In the simplest case, each of the reagents is dissolved in methanol and the solutions preferably combined under a nitrogen blanket. In addition to the bromide-methoxide exchange, one finds that the salt form of the desired alpha-methoxy-4-hydroxyacetophenone is obtained if an alkali metal methoxide or hydroxide or an alkaline earth metal hydroxide is used. The alpha-methoxy-4-hydroxyacetophenone may then be generated by reacting the salt with an acid until a pH of about 6 or less is obtained. The preferred acid is hydrochloric acid, however, virtually any other acid will also suffice. This bromide-methoxide exchange is a surprising result. Tchoubar, *Action des Reacetifs Nucleophiles sur les Cetones Alpha-Halogenees*, Bull. Soc. Chim. (1955), 1362, shows virtually all possible reactions of alpha-chloro ketones. It suggests that the reaction of alpha-chloro ketones in the presence of a strong base such as sodium methoxide produces epoxides and acetals and not a methoxide exchange. In the alternative one may obtain alpha-methoxy-4-hydroxyacetophenone by the method described in *The Synthesis of Anthocyanins*, Journal of the Chemical Society, London (1926), 1, p. 1715, and conduct the reduction step which follows.

Alpha-methoxy-4-hydroxyacetophenone is then catalytically or stoichiometrically reduced to 4-(2'-methoxyethyl)phenol. In the prior art certain ketones may be reduced stoichiometrically by a Wolff-Kischner reaction or Clemmenson Reduction. In the most preferred embodiment the reduction of alpha-methoxy-4-hydroxyacetophenone is conducted by reacting one equivalent of methoxy-4-hydroxyacetophenone with at least two equivalents of hydrogen gas and a catalyst under pressure in an autoclave. In the preferred embodiment, heating is conducted at a temperature of from about 0° C. to about 120° C., more preferably from about 20° C. to about 85° C. The reactor pressure may range from at least about 15 PSIG, more preferably from about 30 PSIG to about 400 PSIG at a reaction time of from about 0.1 to about 6 hours or more preferably from about 0.5 to about 3.0 hours. Useful catalysts include Pd, Pt, Ru, Rh, Raney Nickel and cobalt. Pd/C is the most preferred catalyst at a weight ratio of palladium to carbon in the range of from about 1% to about 10%. The catalyst is preferably present in an amount of from about 0.001 to about 10 grams of catalyst per gram of alpha-methoxy-4-hydroxyacetophenone, or more preferably from about 0.01 to about 2.0 grams and most preferably from about 0.1 to about 1.0 gram of catalyst per gram of alpha-methoxy-4-hydroxyacetophenone. In general, a combination of both catalyst amount and reaction temperatures at the high or low ends of their respective ranges produces an unfavorable yield. A high catalyst amount and low temperature or vice versa produces a good yield. The optimum conditions may be determined by the skilled artisan. It is therefore noted that the preferred catalyst amount and reaction temperature ranges bear an approximately reciprocal relationship. Examples of such ranges are about 0.1–0.3 gram of catalyst per gram of alpha-methoxy-4-hydroxyacetophenone at about 75° C.–85° C. and about 0.9 to 1.0 gram of catalyst per gram of alpha-methoxy-4-hydroxyacetophenone at about 20° C.–25° C., etc. The reduction may preferably be conducted in a solvent which is a carboxylic acid, most preferably acetic acid.

The following non-limiting examples serve to illustrate the invention.

EXAMPLE 1

Bromination of 4-hydroxyacetophenone $CuBr_2$ (22.2 g, 0.1 mol) is heated in 50 ml. ethyl acetate. 4-Hydroxyacetophenone (8.2 g, 0.06 mol) is dissolved in 50 ml of ethyl acetate and 50 ml of chloroform. After the addition of the 4-hydroxyacetophenone solution to the $CuBr_2$ solution, the mixture is refluxed for one hour. A color change from green to pink is noticed. Stripping of solvents leaves 10.8 g of a brown solid. GC/MS analysis finds only alpha-bromo-4-hydroxyacetophenone and residual 4-hydroxyacetophenone. This provides approximately a 76% yield with respect to $CuBr_2$.

EXAMPLE 2

Bromination of 4-hydroxyacetophenone 4-hydroxyacetophenone (136.2 g, 1.0 mol) is dissolved in 1 liter of ethyl acetate and 200 ml of chloroform with stirring to produce a very light yellow solution. Bromine (159.8 g, 1.0 mol) is dissolved in 1 liter of ethyl acetate and 500 ml of chloroform and the bromine solution is slowly added to the 4-hydroxyacetophenone at about 2 ml per minute. Starting at 21.4° C. an amber solution is noticed. After 1¼ hours, 1.2 g of aluminum chloride are added. The addition is complete after 8½ hours. The reaction mixture is filtered. The filtrate is placed on a rotovap at 155 mm and 60° C. to strip off chloroform and ethyl acetate. 221 g of a wet very dark purple residue is observed. The residue is scraped into a flask and 1,320 ml of toluene are added. The flask is equipped with a condenser and mechanical stirrer. Heating is begun and at 85° C., 50 g of carbon and 50 g of Celite are added to the mixture. The mixture is refluxed for 30 minutes at 98° C. The hot mixture is poured into a 105° C. heated funnel. An off-white precipitate forms during the cooling of the yellow filtrate. The solid precipitate is vacuum dried at 0.5 mm at room temperature, 122.9 g of alpha-bromo-4-hydroxyacetophenone (95% purity) are formed.

EXAMPLE 3

Preparation of alpha-methoxy-4-hydroxyacetophenone 2 g of alpha-bromo-4-hydroxyacetophenone are dissolved in 11 g of methanol. 30 g of a saturated solution of sodium hydroxide in methanol (1 g NaOH/ 4.2 ml methanol) is added dropwise to the alpha-bromo-4-hydroxyacetophenone solution. After the addition is complete, the solution is added to 30 g of ice and acidified to pH 6. Alpha-methoxy-4-hydroxyacetophenone precipitates out and is filtered and dried to a greenish yellow product in about 85% yield; the product is determined by 1-H-NMR to be substantially pure.

EXAMPLE 4

Preparation of alpha-methoxy-4-hydroxyacetophenone

In a nitrogen purged glove bag, 35.06 g (95%; 155 mmol) alpha-bromo-4-hydroxyacetophenone, dissolved in 350 ml methanol, are slowly added to a stirred solution of 69.9 g (91.29 mol) sodium methoxide in 660 ml methanol. About 40 minutes after the addition is complete, a solid (NaBr) precipitates out. After 2 hrs, the dark orange mixture is stripped of solvent. The yellow-orange residue is dissolved in 750 ml water. Once the pH is adjusted to 6, the aqueous solution is extracted by 3×250 ml ethyl acetate; the organic phase is dried over $MgSO_4$ and the solvent is removed by roto-evaporation.

The solid is then recrystallized from 180 ml boiling toluene (1.4 g carbon added) to give a light yellow material identified as alpha-methoxy-4-hydroxyacetophenone by GC, $^1$H and $^{13}$C NMR.

Purity: 96.8% (GC)

Yield: 23.3 g=88% with respect to alpha-bromo-4-hydroxyacetophenone.

EXAMPLE 5

Hydrogenation of alpha-methoxy-4-hydroxyacetophenone:

A 300 ml Fluitron autoclave (Hastelloy C) is charged with 1 g alpha-methoxy-4-hydroxyacetophenone (95.9%, 5.8 mmol), 80 ml acetic acid and 0.3 g Pd/C (5% Pd on carbon; 47.8% H$_2$O). After sealing, the stirrer is started, and the autoclave purged with nitrogen and hydrogen and finally pressurized to 250 psig H$_2$. After reaching the reaction temperature of 80° C., the H$_2$ pressure is kept constant at 300 psig over the 2 hour reaction period. The autoclave is vented and purged with N$_2$. The reaction mixture is removed from the reactor, filtered and finally analyzed by GC, using independently made 4-(2'-methoxyethyl)phenol as an external standard.

Yield: 0.54 g (3.6 mmol=61%) 4-(2'-methoxyethyl)phenol, 0.23 g (1.5 mmol=25%) 4-(2'-methoxyethyl)cyclohexanol (estimation, using the GC response factor of 4-(2'-methoxyethyl)phenol)

The experiments listed in Table I are performed according to this procedure, except for the different reaction parameters as specified.

TABLE I

| Solvent | time hrs. | Weight (g) (Pd/C-5%) | P (H$_2$) psig | Temp °C. | Yield (1) mol % | Yield (2) mol % |
|---|---|---|---|---|---|---|
| HOAc | 3 | 0.1 | 300 | 80 | 56 | 0 |
| HOAc | 3 | 0.1 | 30 | r.t. | 0 | 0 |
| HOAc | 3 | 0.55 | 170 | 55 | 64 | 25 |
| HOAc | 3 | 0.55 | 170 | 55 | 61 | 26 |
| HOAc | 3 | 1.0 | 300 | r.t. | 60 | 0 |
| HOAc | 3 | 1.0 | 30 | 80 | 0 | 84 |
| HOAc | 3 | 0.1 | 300 | r.t. | 0 | 0 |
| HOAc | 3 | 1.0 | 30 | r.t. | 73 | 0 |
| HOAc | 3 | 1.0 | 30 | r.t. | 73 | 4 |
| HOAc | 3 | 0.1 | 30 | 80 | 47 | 0 |
| HOAc | 3 | 1.0 | 300 | 80 | 0 | 83 |
| HOAc | 3 | 0.3 | 300 | 80 | 50 | 38 |
| HOAc | 3 | 0.3 | 300 | 80 | 50 | 38 |
| EtOH | 3 | 0.3 | 300 | 80 | 26 | 1 |
| HOAc | 2 | 0.3 | 300 | 80 | 61 | 25 |
| HOAc | 1.4 | 0.3 | 300 | 80 | 75 | 15 |

1 g alpha-methoxy-4-hydroxyacetophenone, (95.9% = 5.8 mmol); 80 ml solvent.
(1) 4-(2'-methoxyethyl)phenol
(2) 4-(2'-methoxyethyl)cyclohexanol
The difference to 100% is due to unidentified products.

What is claimed is:

1. A method for producing 4-(2'-methoxyethyl)phenol which comprises the sequential steps of
    a) brominating 4-hydroxyacetophenone to produce alpha-bromo-4-hydroxyacetophenone, and
    b) causing a methoxide-bromide exchange to the alpha-bromo-4-hydroxyacetophenone to thereby produce alpha-methoxy-4-hydroxyacetophenone;
    c) conducting a single step reduction of alpha-methoxy-4-hydroxyacetophenone with at least two equivalents of hydrogen per equivalent of alpha-methoxy-4-hydroxyacetophenone in the presence of a hydrogenation catalyst to thereby directly produce 4-(2'-methoxyethyl)phenol in a major amount.

2. The method of claim 1 wherein step (a) is conducted with CuBr$_2$ or Br$_2$.

3. The method of claim 1 wherein step (b) is conducted by reacting alpha-bromo-4-hydroxyacetophenone with NaOCH$_3$ and subsequent reaction with an acid.

4. The method of claim 1 wherein step (b) is conducted by reacting alpha-bromo-4-hydroxyacetophenone with methanol plus a component selected from the group consisting of alkali metal hydroxides, alkaline earth metal hydroxides, and alkali metal sulfonates; and subsequent reaction with an acid if an alkali or alkaline earth metal hydroxide is selected.

5. The method of claim 3 wherein the acid is hydrochloric acid in an amount sufficient to provide a pH of about 6 or less.

6. The method of claim 4 wherein the acid is hydrochloric acid in an amount sufficient to provide a pH of about 6 or less.

7. The method of claim 1 wherein step (c) is conducted with a Pd/C catalyst.

8. The method of claim 7 wherein the weight ratio of Pd to C ranges from about 1% to about 10%.

9. The method of claim 1 wherein step (c) is conducted with a component selected from the group consisting of Pd, Pt, Ru, Rh, Raney Nickel and cobalt.

10. The method of claim 1 wherein step (c) is conducted at a pressure of at least 15 PSIG.

11. The method of claim 1 wherein the catalyst is present in an amount of from about 0.001 to about 10.0 grams per gram of alpha-methoxy-4-hydroxyacetophenone.

12. The method of claim 1 wherein step (c) is conducted at a temperature of from about 0° C. to about 120° C.

13. The method of claim 1 wherein step (c) is conducted at a pressure of from about 30 to about 400 PSIG.

14. The method of claim 1 wherein step (c) is conducted at a temperature of from about 20° C. to about 85° C.

15. The method of claim 1 wherein step (c) is conducted with a carboxylic acid solvent.

16. The method of claim 15 wherein step (c) is conducted with acetic acid as the solvent.

17. A method for producing 4-(2'-methoxyethyl)phenol which comprises the sequential steps of
    a) providing alpha-methoxy-4-hydroxyacetophenone;
    b) conducting a single step reduction of alpha-methoxy-4-hydroxyacetophenone by reaction with at least two equivalents of hydrogen per equivalent of alpha-methoxy-4-hydroxyacetophenone in the presence of a hydrogenation catalyst to thereby directly produce 4-(2'-methoxyethyl)phenol in a major amount.

18. The method of claim 17 wherein step (b) is conducted with a Pd/C catalyst.

19. The method of claim 17 wherein step (b) is conducted with a component selected from the group consisting of Pd, Pt, Ru, Rh, Raney Nickel and cobalt.

20. The method of claim 17 wherein step (b) is conducted at a pressure of at least 15 PSIG.

21. The method of claim 17 wherein step (b) is conducted at a pressure of from about 30 to about 400 PSIG.

22. The method of claim 17 wherein step (b) is conducted at a temperature of from about 0° C. to about 120° C.

23. The method of claim 17 wherein step (b) is conducted with a carboxylic acid solvent.

24. The method of claim 23 wherein step (b) is conducted with acetic acid as the solvent.

25. The method of claim 17 wherein the catalyst is present in an amount of from about 0.001 to about 10.0 grams per gram of alpha-methoxy-4-hydroxyacetophenone.

26. The method of claim 17 wherein step (b) is conducted at a temperature of from about 20° C. to about 85° C.

* * * * *